United States Patent [19]

Matysiak

[11] Patent Number: 5,026,361
[45] Date of Patent: Jun. 25, 1991

[54] POST-OPERATIVE FITTING DEVICE FOR A LATERAL COLOSTOMY

[76] Inventor: Lucien Matysiak, 32 rue Henri Lebert, 68000 Colmar, France

[21] Appl. No.: 391,421

[22] Filed: Aug. 9, 1989

[30] Foreign Application Priority Data

Aug. 10, 1988 [FR] France .................. 88 10905

[51] Int. Cl.⁵ .............................................. A61F 5/44
[52] U.S. Cl. .................................. 604/338; 604/332; 604/337; 604/342; 604/343
[58] Field of Search ............... 604/332, 338, 344, 337, 604/339, 342, 353, 345, 277, 135, 343; 24/697, 662

[56] References Cited

U.S. PATENT DOCUMENTS 2,837,094  6/1958  Cowles .................. 604/338

FOREIGN PATENT DOCUMENTS 81907    6/1983  European Pat. Off. .
2193439  2/1988  United Kingdom ........ 604/332
2198953  6/1988  United Kingdom ........ 604/332

Primary Examiner—David J. Isabella
Attorney, Agent, or Firm—Ostrolenk, Faber, Gerb & Soffen

[57] ABSTRACT

A device for a side colostomy post-operation installation includes a pair of half-rings. The half-rings include tenons and mortises which fit together to form a ring. The device also includes a solid tube segment and a hollow tube segment which fit together to form a rod.

7 Claims, 3 Drawing Sheets

POST-OPERATIVE FITTING DEVICE FOR A LATERAL COLOSTOMY

BACKGROUND OF THE INVENTION

The object of the present invention concerns a post-operation fitting device for a side colostomy commonly called "on rod".

We known of many different types of "rods" allowing to maintain the colon in place after externalization.

Some of these "rods" consist of fragments of rubber or silicone tubes, others are made of glass but all present the major inconvenience that they require a fixation on the skin on each side of the intestine, such fixation being ofter performed with a thread. In addition these "rods" render difficult the installation of a pouch because they require more or less important cut-outs in the cutaneous protection on which this pouch is generally fixed, whose effect is to hinger the system sealing.

The purpose of the present invention is to remedy the various known system inconveniences by proposing a device that combines the easiness of installation, with the essential advantage, which is not to require fixation points on the skin, as well as that of presenting a perfect sealing, totally non-traumatic for the colon and easily replaceable, in opposition to the "rods" directly fixed onto the skin.

SUMMARY OF THE INVENTION

The device in accordance with the invention is essentially characterized in that it presents two semi-circular parts made of plastic which fit together, one into the other, by a mortise and tenon joint and which are each equipped in their center with two tubular segments of approximately semi-circular section, which fit together one into the other, one of which being solid makes-up the male part of the assembly whereas the other being hollow makes-up the female part of the assembly forming the whole said ring-shaped device.

The two semi-circular parts of the device in accordance with the invention are each equipped on their lower side with a self adhesive protective cutaneous half-ring made of flexible plastic material such as acrylic resin and extended on the outside of each half-ring by a shoulder made of micro-porous adhesive which reinforces the adherence of the assembly to the skin.

In addition, the two half-rings of the device in accordance with the invention are equipped on the outside edge of their upper side with an overhanging lip allowing the installation of a collecting pouch by simple pressure, due to a snap-on fit-together system. For this purpose, the collective pouch is equipped with a plastic ring relatively flexible capable of being inserted below the lip of the ring assembly made-up of the two half-rings. This ring will be sufficiently flexible to allow removing of the collective pouch without excessive pulling on the device, to avoid injury to the colon.

Other features and advantages of the present invention will become apparent from the following description of preferred embodiments of the invention, with reference to the accompanying drawings.

BRIEF DESCRIPTION OF THE DRAWINGS

Other details and advantages of the invention will appear more clearly at the reading of the detailled description that follows concerning a manufacturing mode of the device in accordance with the invention, being understood that this description does not present any limitative character toward the invention.

The descriptions that follow refer to the drawings in annex that is to say.

DETAILED DESCRIPTION OF THE PREFERRED EMBODIMENTS OF THE INVENTION

Figure 1:
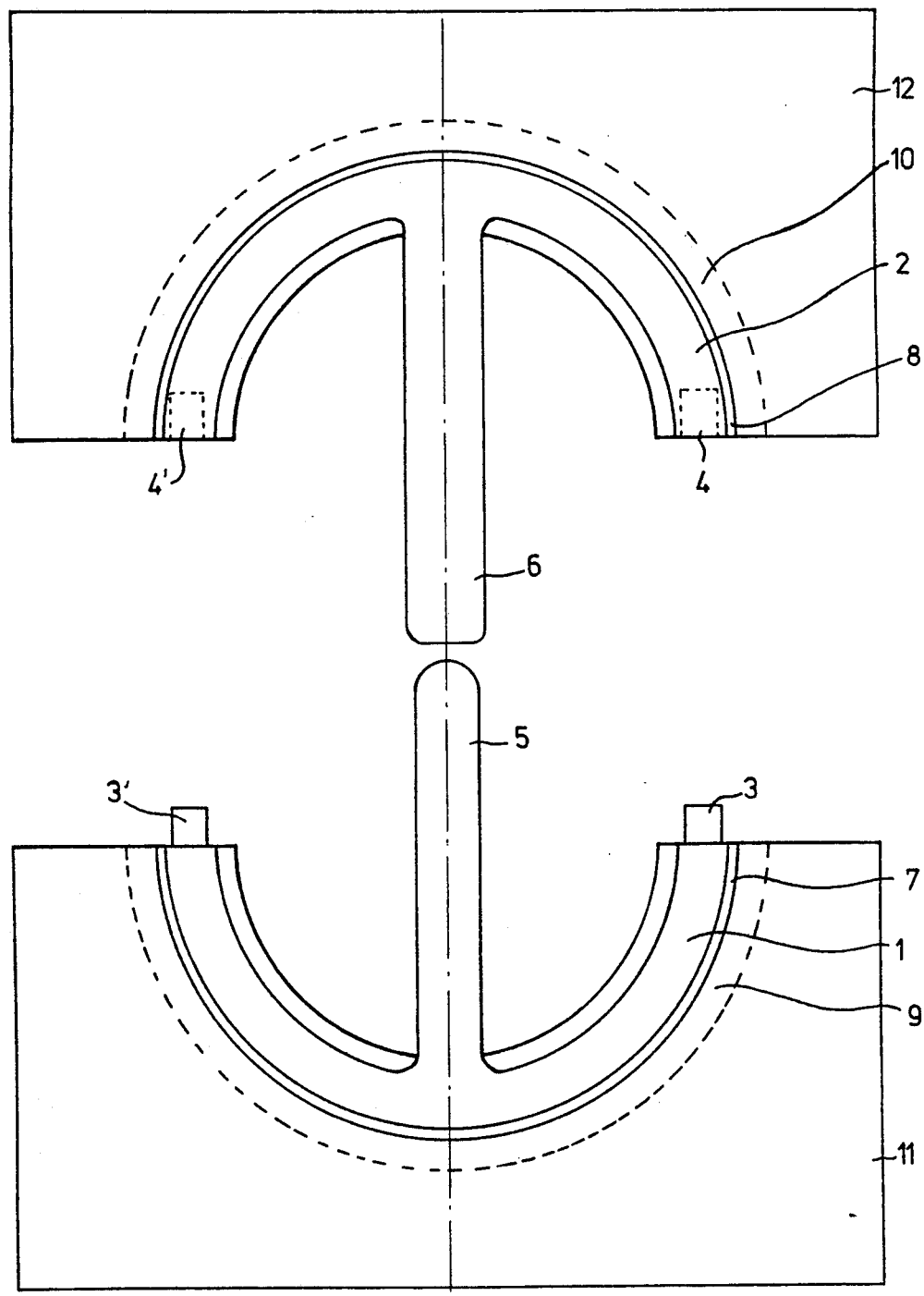
FIG. 1 represents an overhead view of the device in accordance with the invention in the "open" position.

When referring to FIG. 1, we see that a preferred embodiment of the invention consists of two half-rings (1) and (2), the half-ring (1) being extended at its ends by two tenons (3—3') capable of being inserted in the two mortises (4—4') provided at the ends of the half-ring (2).

The half-ring (1) is extended in its center by a solid tube element (5) to be introduced in the hollow tube element (6) of the corresponding section, extending the half-ring (2) in its center.

Each of the half-rings (1) and (2), presents on the exterior edge of its upper side a chamfer refectively (7) and (8) to facilitate the installation of the ring completing the collective pouch, not represented.

On their lower side, the half-rings (1) and (2) in addition are each equipped with an adhesive protective half-ring, respectively (9) and (10), which overlap each half-ring and is extended by a half-shoulder, respectively (11) and (12) made of a micro-porous adhesive.

Figure 2:
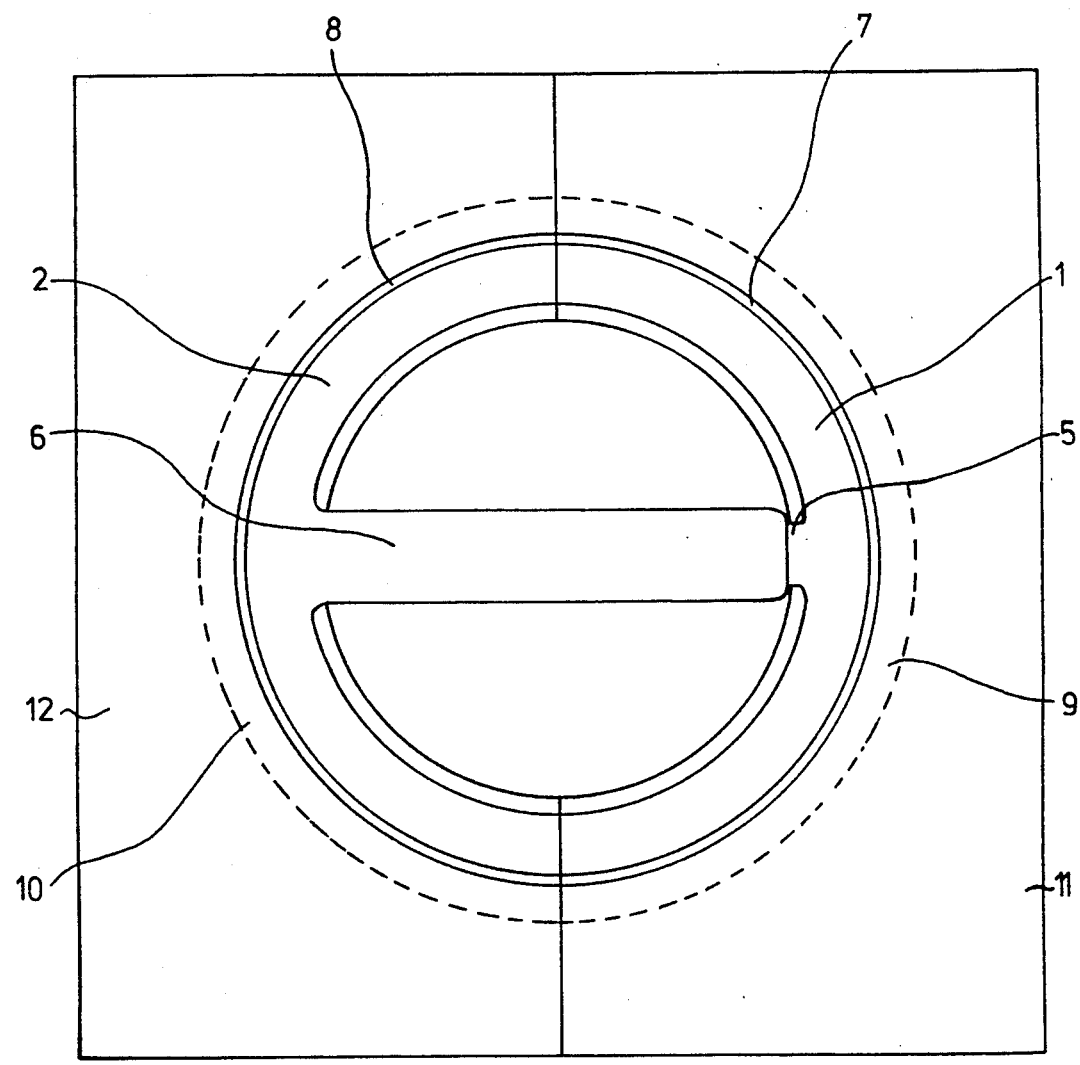
FIG. 2 represents an overhead view of the same device in the "closed" position.

FIG. 2 illustrates the various elements of FIG. 1, the two half-rings (1) and (2) forming only one ring and the tube segments (5) and (6) forming the rod of the device. The two protective half-rings (9) and (10), combined also form only one protective ring and in the same manner the half-shoulders (11) and (12) form one continuous shoulder assuring a better fixation of the assembly.

Figure 3A:
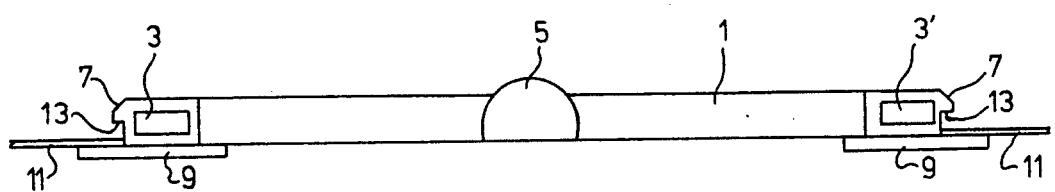
FIG 3a represents a side view of the half-ring of the preceeding figures which include the male assembling elements.

FIG. 3a illustrates the half-ring (1) fitted on its ends with the tenons (3) and (3') and in its center with a solid tube segment (5). The exterior edge of its upper side is fitted with a chamber (7) and edge lip (13) foreseen to maintain the ring completing the collective pouch, not represented.

On its lower side, the half-ring (1) is equipped with an adhesive protective half-ring (9) beyond which extends an adhesive micro-porous half-shoulder (11).

Figure 3B:
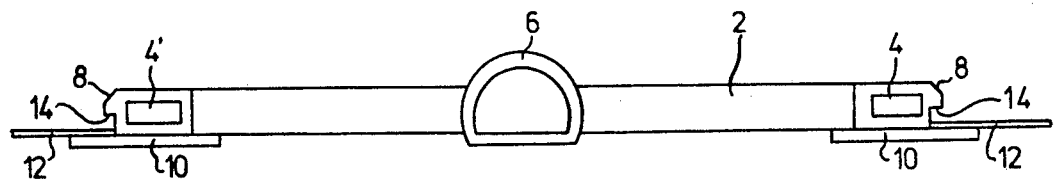
FIG. 3b represents a side view of the half-ring of the preceeding figures which include the female assembling elements.

FIG. 3b illustrates the half-ring (2) provided on its ends with the mortises (4) and (4') and in its center with the hollow tube segment (6). The exterior edge of its upper side is equipped with a chamfer (8) and an edge lip (14) foreseen to maintain the ring completing the collective pouch, not represented.

On its lower side, the half-ring (2) is equipped with an adhesive protective half-ring (10) beyond which extends an adhesive micro-porous half-shoulder (12).

The installation of this device is preformed in a simpler manner: once the colon is externalized, the rubber tube which was used for this purpose is replaced by the female tube segment (6) extended by the half-ring 2. Once this element is in place, the male element of the device is adapted on it. The skin being perfectly dry, we remove the protective paper from the adhesive protective half-rings (9) and (10) as well as from the adhesive half-shoulders (11) and (12) and we apply the assembly on the skin, then we adapt to the ring (1)–(2) a receptive pouch using the flexible plastic ring which completes and comes to fasten itself under the edge lip (13–14) of the ring (1–2).

The replacement of the device in accordance with the invention is also performed in a simple manner by first removing the female half of the device and by applying, after cleaning the skin, a new female half which we fasten immediately after removing the protective paper from its adhesive parts. We then proceed in the same manner for the replacement of the male part of the device.

The device in accordance with the invention, as stated previously, presents the considerable advantage that it does not require fixation by points of the skin onto the rod it has in its center and which is perfectly maintained in place by the half-rings on which it is fixed.

In addition, the approximate half-circle section of the rod is non-traumatic for the colon, which it does not risk to cut, while assuring sufficient seating for the skin.

The device in accordance with the invention, as stated previously, also presents the advantage of being easily replaceable at all times, in opposition to the rods fixed into the skin by points, which confers it the supplement advantage of cleanliness.

The adhesive protective ring-shoulder assembly assures a perfectly sealed assembly, due to the particularity that the fixation of the rod to the ring made of the assembly of the half-rings does not require more or less important cut-outs, always difficult, of the protective disc fixed onto the skin.

The two half-rings of the device in accordance with the invention, with their center parts, are easily made by semi-rigid plastic moulding, such as a thermoplastic resin of polyvinylic type or a silicone, in such a manner that the center rod resists the traction of the colon, to the holding of which also participate the two half-rings.

The device in accordance with the invention can also be made in different adaptable sizes, in particular to the different colostomy sizes.

Although the present invention has been described in connection with particular embodiments thereof, many other variations and modifications and other uses will become apparent to those skilled in the art. It is preferred, therefore, that the present invention be limited not by the the specific disclosure herein, but only by the appended claims.

I claim:

1. A device for a side colostomy post-operation installation, the device comprising:
   a male half-ring terminating into opposite ends, an external edge and a center, each of the ends including tenons, the external edge including an overhanging edge lip;
   a female half-ring terminating into opposite ends, an external edge and a center, each of the ends of the female half-ring including mortises, the external edge of the female half-ring including an overhanging edge lip, wherein the tenons are configured to fit together with the mortises to form a ring, wherein the ring having a diameter;
   a solid tubular segment which extends from the center of the male half-ring;
   a hollow tubular segment which extends from the center of the female half-ring, the hollow tubular segment having a length which is approximately equal to the diameter of the ring; and configured to slidably engage said solid tubular segment; and
   a first adhesive cutaneous protective half-ring which is located on a lower side of the male half-ring, the first protective half-ring extending inwardly beyond a radially inner side and outwardly beyond a radially outer side of the male half-ring, a second adhesive cutaneous protective half-ring which is located on a lower side of the female half-ring, the second protective half-ring inwardly beyon a radially inner side and outwardly beyond a radially outer side of the female half-ring, the first and second half-rings being larger than the ring, a first half shoulder of micro-porous adhesive which extends exteriorly away from the first protective half-ring and a second half shoulder of micro-porous adhesive which extends exteriorly away from the second protective half-ring.

2. The device of claim 1, wherein each of the external edges includes a chamfer for installing a collection pouch onto the ring.

3. The device of claim 1, wherein each of the tubular segments has an approximately semi-circular cross-section.

4. The device of claim 1, wherein the male and female half-rings and the tubular segments are formed of semi-rigid plastic material.

5. The device of claim 4, wherein the plastic material is selected from the group consisting of silicones and thermoplastic polvinyl resins.

6. The device of claim 4, wherein the protective half-rings are formed of flexible plastic material.

7. The device of claim 6, wherein the flexible plastic material includes acrylic resin.

* * * * *